(12) United States Patent
Chu

(10) Patent No.: US 6,235,055 B1
(45) Date of Patent: May 22, 2001

(54) INTRAOCULAR LENS HAVING COLORED HAPTICS FOR ANTERIOR/POSTERIOR ORIENTATION, AND METHOD FOR IMPLANTING IT

(76) Inventor: Milton W. Chu, 11887 Ellice, Unit #5, Malibu, CA (US) 90265

(*) Notice: Subject to any disclaimer, the term of this patent is extended or adjusted under 35 U.S.C. 154(b) by 0 days.

(21) Appl. No.: 09/370,840

(22) Filed: Aug. 9, 1999

(51) Int. Cl.$^7$ .................................................. A61F 2/16
(52) U.S. Cl. ............................................................ 623/6.48
(58) Field of Search ................................ 623/6.48, 6.5, 623/6.11, 6.17, 6.38–6.56, 6.62

(56) References Cited

U.S. PATENT DOCUMENTS

| | | |
|---|---|---|
| 4,298,994 | 11/1981 | Clayman . |
| 4,718,905 * | 1/1988 | Freeman ................................ 623/6.5 |
| 4,841,653 | 6/1989 | Negley . |
| 4,932,967 | 6/1990 | Kansas . |
| 4,961,746 | 10/1990 | Lim et al. . |
| 5,074,942 | 12/1991 | Kearns et al. . |
| 5,207,708 | 5/1993 | Blumenthal . |
| 5,252,262 | 10/1993 | Patel . |
| 5,405,386 | 4/1995 | Rheinish et al. . |
| 5,549,669 | 8/1996 | Jansen . |
| 5,713,300 | 2/1998 | Hubert . |

FOREIGN PATENT DOCUMENTS

99/29265 * 6/1999 (WO) ........................... 623/FOR 105

* cited by examiner

*Primary Examiner*—David H. Willse
(74) *Attorney, Agent, or Firm*—Sheppard, Mullin, Richter & Hampton LLP; James R. Brueggemann

(57) ABSTRACT

An intraocular lens incorporating a central lens optic and a plurality of haptics, e.g., flexible haptic arms or haptic plates, having anterior and posterior sides that are visually distinguishable from each other. For example, the anterior and posterior sides of the haptics can have contrasting colors or textures. This reduces the possibility that the intraocular lens might mistakenly be implanted in a reversed orientation, with its anterior side facing rearwardly and its posterior side facing forwardly.

9 Claims, 2 Drawing Sheets

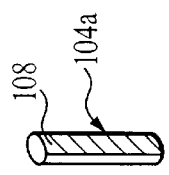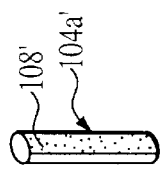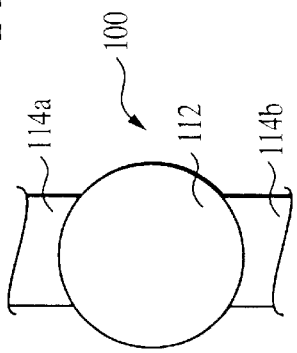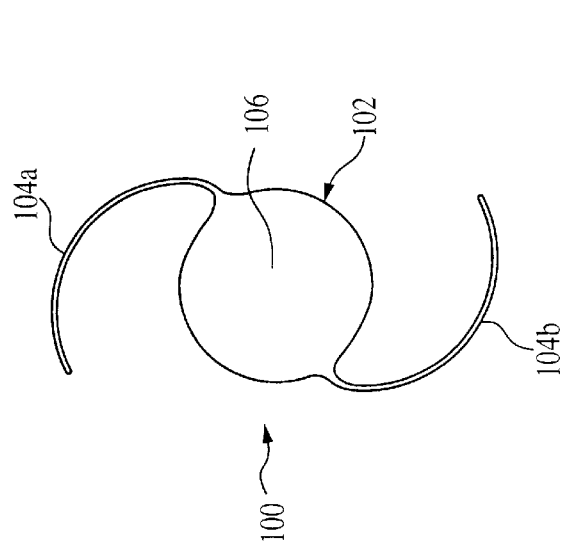

INTRAOCULAR LENS HAVING COLORED HAPTICS FOR ANTERIOR/POSTERIOR ORIENTATION, AND METHOD FOR IMPLANTING IT

BACKGROUND OF THE INVENTION

1. Field of the Invention

This invention relates generally to intraocular lenses and, more particularly, to intraocular lenses having fixation arms specially configured to facilitate proper implantation.

2. Description of the Related Art

FIG. 1 is a cross-sectional view of a normal human eye 10, which has a generally spherical body defined by an outer wall called the sclera 12 and a transparent bulbous front portion called the cornea 14. A lens 16 is located within the spherical body, behind the cornea, and an iris 18 is located between the lens and the cornea, dividing the eye into an anterior chamber 20 in front of the iris and a posterior chamber 22 in back of the iris. A central opening in the iris, called the pupil 24, controls the amount of light that reaches the lens. Light is focused by the cornea and the lens onto a retina 26 at the rear of the eye.

The lens 16 is a biconvex, highly transparent structure surrounded by Et thin lens capsule 28. The lens capsule is supported at its periphery by suspensory ligaments called zonules 30, which are continuous with the ciliary muscle 32. The ciliary muscle functions to change the focal length of the lens. Immediately in front of the zonules, between the ciliary muscle and iris 18, is a region referred to as the cilify sulcus 34.

A cataract condition results when the lens 16 becomes clouded, thereby obstructing the passage of light. To correct this condition, three alternative forms of surgery have been used, including intracapsular extraction, extracapsular extraction, and phacoemulsification. In intracapsular cataract extraction, the zonules 30 around the entire periphery of the lens capsule 28 are severed, and the entire lens structure, including the lens capsule, is then removed. In extracapsular cataract extraction and phacoemulsification, only the clouded material within the lens capsule is removed, while the transparent posterior lens capsule wall 28a with its peripheral portion, as well as the zonules, remain in the eye.

Intracapsular extraction, extracapsular extraction, and phacoemulsification all eliminate the light blockage caused by the cataract condition. However, light entering the eye thereafter is not properly focused onto the retina 26. A contact lens can be placed on the exterior surface of the eye, but this approach has the disadvantage that the patient has virtually no useful sight when the contact lens is removed. A preferred alternative is to implant an artificial lens, known as an intraocular lens (IOL), directly within the eye.

IOLs typically incorporate a disk-shaped, transparent lens optic and two smoothly curved attachment arms referred to as haptics. The lens optic typically is formed of a polymeric material such as polymethyl methacrylate, which is suitable for lathe turning or molding by injection, compression or cast molding techniques. The IOL is implanted through an incision made near the periphery of the cornea, which may be the same incision as is used to remove the cataract. The IOL is implanted either in the eye's anterior chamber, in front of the iris, or in the eye's posterior chamber, in back of the iris.

Anterior chamber IOLs can be supported by contact of the haptics with the iris 18 or with the anterior chamber angle, formed at the union of the iris and the cornea 14. Posterior chamber IOLs, on the other hand, can be supported by several alternative techniques. In one such technique, the IOL is placed in the sack-like structure formed by the intact posterior and peripheral walls of the lens capsule 28, where the haptics compress slightly against the periphery of the lens capsule, to hold the IOL in place. In another technique, the IOL is placed in front of and outside the lens capsule, where the haptics compress slightly against the ciliary sulcus 34. In yet another technique, the IOL is secured in place by suturing the haptics to the ciliary sulcus or to the iris.

The lens optics of many IOLs now are formed of materials that are sufficiently soft and flexible to allow the lens optic to be folded, for insertion into the eye through an incision of reduced size. After insertion, the lens is unfolded and positioned within the eye in a normal manner, e.g., with its haptics engaging the lens capsule, the ciliary sulcus, the iris, and/or the anterior chamber angle.

Many IOLs are asymmetric along their optical axes, perpendicular to the plane of the lens optic. For example, the haptics of posterior chamber IOLs frequently are angulated slightly in the anterior direction from the lens optic's plane. This angulation increases the spacing between the lens optic and the iris and thereby minimizes possible interference. In addition, the posterior and anterior surfaces of the IOLs typically are not identically shaped; each surface is uniquely shaped to achieve the desired optical correction.

Despite the asymmetry of many IOLs along their optical axes, it is sometimes difficult for the eye surgeon to visually differentiate the IOLs anterior and posterior sides. Consequently, the IOL occasionally can be improperly implanted in a reversed orientation within the eye, i.e., with its anterior side facing rearwardly and its posterior side facing forwardly. This reversal can adversely affect the optical correction provided by the IOL, and it can lead to problems associated with unwanted interaction with other eye tissue, including, for example, interference with the iris.

It should, therefore, be appreciated that there is a need for an IOL configured to minimize the possibility of improperly implanting it in a reverse orientation within the eye, with its anterior side facing rearwardly and its posterior side facing forwardly. The present invention fulfills this need.

SUMMARY OF THE INVENTION

The present invention is embodied in an intraocular lens (IOL) configured for implantation into an eye, the IOL incorporating a central lens optic and a plurality of fixation arms or haptics projecting outwardly therefrom, at least one of such haptics being configured with its anterior and posterior sides having contrasting appearances. The two sides of the IOL thereby can be readily distinguished from each other, which reduces the possibility of improperly implanting the IOL in a reversed orientation, with its anterior side facing rearwardly and its posterior side facing forwardly. The invention, thereby, minimizes the risk of creating errors in optical correction and/or undesired interference with other eye tissue, which could occur from improperly implanting the IOL.

In more detailed features of the invention, the contrasting appearances for the anterior and posterior sides of the haptics can take the form of contrasting colors and/or textures. The contrasting appearances can extend along either the entire length of each haptic or, alternatively, along only a portion of each haptic's length. The haptics can be of any suitable form, typically projecting outwardly from diametrically opposite sides of the central lens optic.

Other features and advantages of the present invention should become apparent from the following description of the preferred embodiments, taken in conjunction with the accompanying drawings, which illustrate, by way of example, the principles of the invention.

BRIEF DESCRIPTION OF THE DRAWINGS

FIG. 3 is a plan view of the IOL of FIG. 2.

FIG. 4 is a side elevational view of the IOL of FIG. 2.

FIG. 5 is an enlarged, fragmentary view of a portion of one of the haptics of the IOL of FIG. 2, the view showing the haptic's anterior side to have a color that contrasts with that of the haptic's posterior side.

FIG. 6 is an enlarged, fragmentary view of a portion of a haptic of an alternative embodiment of an IOL in accordance with the invention, the view showing the haptic's anterior side to have a texture that contrasts with that of the haptic's posterior side.

FIG. 7 is a plan view of another alternative embodiment of an IOL in accordance with the invention, incorporating fixation arms in the form of haptic plates having anterior and posterior sides that are visually distinguishable from each other.

DESCRIPTION OF THE PREFERRED EMBODIMENTS

Figure 1:
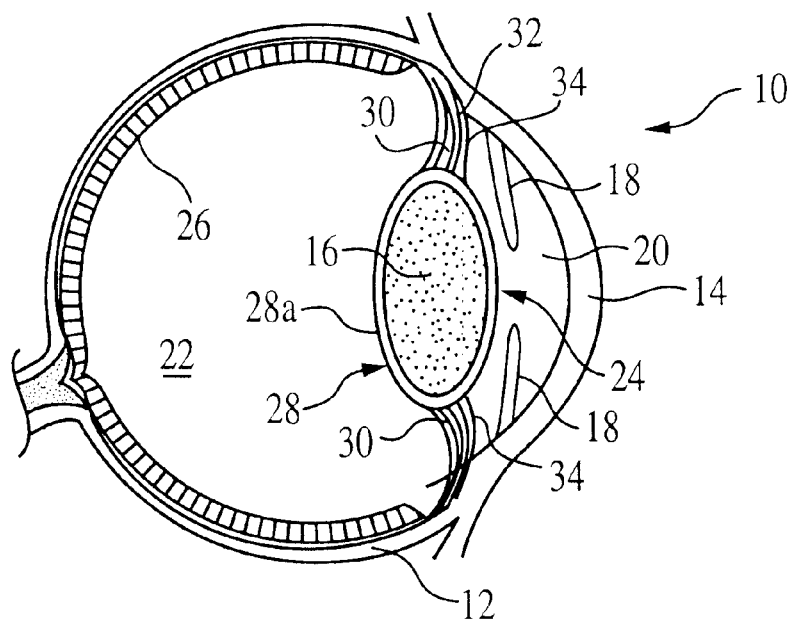
FIG. 1 is a cross-sectional view of a typical healthy human eye.
Figure 2:
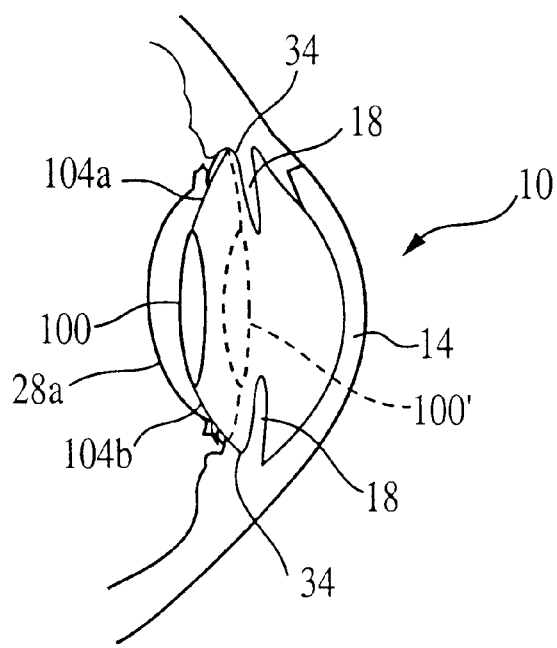
FIG. 2 is a partial cross-sectional view of a human eye in which has been implanted a posterior chamber intraocular lens (IOL) in accordance with the invention, with a proper orientation of the IOL being depicted in solid lines and an improper, reversed orientation being depicted in phantom lines.

With reference now to the illustrative drawings, and particularly to FIG. 2, there is shown an intraocular lens (IOL) 100 embodying the invention, which has been surgically implanted in the posterior chamber 22 of a human eye 10, behind the eye's iris 18 and pupil 24. The depicted IOL has been implanted as a replacement for the eye's natural lens, which was previously extracted because of a cataract condition. The extraction removed the natural lens' front wall or anterior capsule and, the clouded cellular material within the capsule. Remaining in place within the eye is the natural lens' rear wall or posterior capsule 28a.

As shown in FIGS. 3 and 4, the IOL 100 incorporates a disk-shaped lens optic 102 and first and second haptics 104a and 104b attached at opposite points on the lens optic's periphery. A central region 106 of the lens optic, aligned with the eye's pupil 24 (FIG. 2), functions as an optical corrective zone. The lens optic is depicted to be biconvex in diametric cross-section, with its rear or posterior surface being somewhat more convex than is its forward or anterior surface. Alternatively, the lens optic could be plano-convex, convexo-concave, or plano-concave. Other lens designs also could be used, including multi-focal designs. The lens optic further is depicted to have a peripheral configuration that is substantially circular. Other desirable lens optic configurations alternatively could be used.

The lens optic 102 preferably is formed of a transparent polymeric material, e.g., polymethyl methacrylate, suitable for lathe turning or molding by injection, compression or cast molding techniques. Alternatively, the lens optic could be formed of any of various newer materials that are sufficiently soft and flexible to allow the lens optic to be folded, for insertion into the eye through an incision of reduced size.

The haptics 104a and 104b project outwardly from opposite points on the periphery of the lens optic 102, and they curve smoothly in a circumferential direction so as to constitute long flexible arms. These arms are sized to resiliently engage the eye's lens capsule 28 or ciliary sulcus 34, and thereby center and retain the IOL 100 in its desired position within the eye.

The haptics 104a and 104b preferably are attached to the lens optic's peripheral edge in a manner that minimizes interference with the lens optic 102. This. can be accomplished by providing a bore in the lens optic, by drilling or molding, and then inserting the haptic's base end into the bore. The inserted haptic then can be permanently or removably secured by known adhesive, thermal or mechanical means. Alternatively, the haptics and the lens optic could be formed as a one-piece construction.

The IOL 100 is slightly asymmetric along the lens' optical axis, perpendicular to the plane of the lens optic 102. In particular, and as best observed in FIGS. 2 and 4, the haptics 104a and 104b are each angulated at an angle $\alpha$ forward of the lens optic's plane, i.e., in an anterior direction. This angulation functions to space of the IOL rearwardly of the eye's iris 18 after implantation, thus minimizing the possibility of undesired interference with eye tissue such as the iris.

Unfortunately, the slight angulation of the haptics 104a and 104b relative to the plane of the lens optic 102 is not always readily observable by the surgeon at the time the IOL 100 is being implanted. Consequently, the IOL sometimes can be inadvertently implanted in a reversed orientation, i.e., with its anterior side facing rearwardly and its posterior side facing forwardly. This improper, reversed orientation is depicted by phantom lines 100' in FIG. 2. This has the undesired effect of positioning the IOL with the lens optic sufficiently forward that it can interfere with the iris 18, the ciliary structure, and/or other eye tissue. The improper orientation also can produce various kinds of optical errors.

In accordance with the invention, the possibility of the surgeon mistakenly implanting the IOL 100 in a reversed orientation is reduced substantially by configuring one or both of the haptics 104a and 104b to have anterior and posterior sides that are visually distinguishable from each other. For example, as shown in the detailed view of FIG. 5, one side (e.g., the anterior side) of each haptic can be configured to have a particular color or tint that contrasts with the color or tint of the opposite side. The tinted anterior side of the haptic is identified by the reference numeral 108 in FIG. 5.

The coloration or tinting can be provided in any of several suitable wares.

For example, a suitable dye or tinted plastic coating can be applied to the haptic's exposed anterior surface, either before or after its assembly to the lens optic 102. Tie haptic initially can be either transparent or uniformly tinted in a contrasting color. The coloration can extend along the haptic's entire length or, alternatively, only along a portion of it.

Alternatively, as shown in the detailed view of FIG. 6, one side (e.g., the anterior side) of a haptic 104a' can be configured to have a texture, while the opposite side is smooth. This texture can be provided in any of several suitable ways, e.g., using pressure, heat, a laser, or chemical or mechanical etching. The texture can be provided either before or after the haptic's assembly to the associated lens optic. The texturized anterior side of the haptic is identified by the reference numeral 108' in FIG. 6. The texturization can extend along the haptic's entire length or, alternatively, only along a portion of it.

With reference now to FIG. 7, there is shown a further embodiment of an IOL 110 in accordance with the invention. This IOL incorporates a central lens optic 112 with a pair of haptic plates 114a and 114b projecting from opposite of the lens optic's periphery. IOLs such as this commonly are referred to as plate lenses, and they typically are formed of silicone, or other flexible material, making them suitable for insertion into the eye in a folded state, after which they are unfolded for positioning in their prescribed position. The haptic plates function as fixation arms, engageable with the eye's lens capsule 28, ciliary sulcus 34, and/or anterior chamber angle (FIG. 2), to center and retain the IOL in its prescribed position within the eye.

As with the IOL embodiments depicted in FIGS. 2–6, the IOL 110 of FIG. 7 likewise is configured to enable the surgeon to visually distinguish its anterior and posterior sides, such that the possibility of mistakenly implanting the lens in a reversed orientation is reduced. Specifically, this is achieved by configuring the anterior and posterior sides of the haptic plates 114a and 114b to have contrasting colors or textures. All or just a portion of plates can be configured in this way. The plates can be colored or texturized in a manner similar to that used to color the haptics 104a and 104b of the IOL of FIGS. 2–5 or to texturize the haptic 104a' of FIG. 6.

The IOL embodiments described above all are configured for implantation following cataract extraction. It will be appreciated that IOLs in accordance with the invention also can be used as part of other vision-corrective refractive or reconstructive surgeries. Such other IOLs could be used alone or with other, additional implants.

It should be appreciated from the foregoing description that the present provides an improved IOL, incorporating a central lens optic and haptics, e.g., flexible arms or haptic plates, having anterior and posterior sides that are visually distinguishable from each other. For example, the anterior and posterior sides of the haptics can have contrasting colors or textures. This reduces the possibility that the IOL might mistakenly be implanted in a reversed orientation, with its anterior side facing rearwardly and its posterior side facing forwardly.

Although the invention has been described in detail with reference only to the preferred embodiments, those of ordinary skill in the art will appreciate that various modifications can be made without departing from the invention. Accordingly, the invention is defined only by the following claims.

I claim:

1. An intraocular lens configured for implantation into an eye, comprising:
    a central lens optic defining a plane with an anterior side and a posterior side; and
    a plurality of elongated, flexible-arm haptics projecting outwardly from the central lens optic and configured to engage a predetermined portion of the eye, and thereby to retain the intraocular lens in a predetermined position within the eye, wherein the haptics each have an anterior side and a posterior side;
    wherein the anterior and posterior sides of at least one of the plurality of haptics are configured to have contrasting colors, such that the two sides can be visually distinguished from each other during implantation, thereby facilitating a proper implantation of the intraocular lens within the eye, with its anterior side facing forwardly and its posterior side facing rearwardly.

2. An intraocular lens as defined in claim 1, wherein the anterior and posterior sides of at least one of the plurality of haptics further are configured to have contrasting surface textures.

3. An intraocular lens as defined in claim 1, wherein:
    the plurality of haptics consist of two elongated haptics projecting outwardly from diametrically opposite sides of the lens optic; and
    the anterior and posterior sides of both haptics are configured to have contrasting colors.

4. An intraocular lens as defined in claim 1, wherein the plurality of haptics comprise two elongated haptics having substantially identical configurations.

5. An intraocular lens as defined in claim 1, wherein the plurality of haptics are angulated relative to the plane of the lens optic.

6. An intraocular lens as defined in claim 1, wherein the anterior and posterior sides of at least one of the plurality of haptics are configured to have contrasting colors along substantially the entire length of the haptic.

7. An intraocular lens configured for implantation into an eye, comprising:
    a central, substantially circular lens optic defining a plane with an anterior side and a posterior side; and
    first and second elongated, flexible-arm haptics projecting outwardly from diametrically opposite sides of the central lens optic's periphery, at a slight angle relative to the plane of the lens optic, wherein the haptics each have an anterior side and a posterior side, and wherein the haptics are configured substantially identical to each other and are configured to engage a predetermined portion of the eye, to retain the intraocular lens in a predetermined position within the eye;
    wherein the anterior and posterior sides of both of the first and second haptics are configured to have contrasting colors, such that the two sides can be visually distinguished from each other during implantation, thereby facilitating a proper implantation of the intraocular lens within the eye, with its anterior 15 side facing forwardly and its posterior side facing rearwardly.

8. An intraocular lens as defined in claim 7 wherein the anterior and posterior sides of the first and second haptics further are configured to have contrasting surface textures.

9. A method for implanting an intraocular lens, comprising:
    providing an intraocular lens having
        a central lens optic defining a plane with an anterior side and a posterior side, and
        a plurality of elongated, flexible-arm haptics projecting outwardly from the central lens optic, wherein the haptics each have an anterior side and a posterior side, and wherein the anterior and posterior sides of at least one of the plurality of haptics are configured to have contrasting colors, such that the two sides can be visually distinguished from each other; and
    implanting the intraocular lens within an eye, with the plurality of haptics engaging a predetermined portion of the eye, to retain the intraocular lens in a predetermined position within the eye;
    wherein implanting includes relying on the contrasting colors of the anterior and posterior sides of at least one of the plurality of haptics to aid in orienting the lens with its anterior side facing forwardly and its posterior side facing rearwardly.

* * * * *

UNITED STATES PATENT AND TRADEMARK OFFICE
CERTIFICATE OF CORRECTION

PATENT NO. : 6,235,055 B1  Page 1 of 1
DATED : May 22, 2001
INVENTOR(S) : Milton W. Chu M.D.

It is certified that error appears in the above-identified patent and that said Letters Patent is hereby corrected as shown below:

Column 1,
Line 25, "Et" should be -- a --.
Line 30, "cilify" should be -- ciliary --.

Column 4,
Line 22, "eye¹s" should be -- eye's --.
Line 49, this sentence should be at the beginning of the next paragraph.
Line 50, "wares" should be -- ways --.
Line 53, "Tie" should be -- The --.

Column 5,
Line 31, "invention" has been deleted.

Column 6,
Line 38, "15" has been added.

Signed and Sealed this

Nineteenth Day of February, 2002

Attest:

Attesting Officer

JAMES E. ROGAN
Director of the United States Patent and Trademark Office